United States Patent [19]

Wilson

[11] Plant 4,464

[45] Oct. 16, 1979

[54] FRUITLESS OLIVE TREE

[76] Inventor: Richard P. Wilson, 260 Cranston Crest, Escondido, Calif. 92025

[21] Appl. No.: 930,865

[22] Filed: Aug. 3, 1978

[51] Int. Cl.[2] ..... A01H 5/03

[52] U.S. Cl. ..... Plt./33

[58] Field of Search ..... Plt./33

*Primary Examiner*—Robert E. Bagwill

*Attorney, Agent, or Firm*—Lyon & Lyon

[57] ABSTRACT

A new and distinct variety of olive tree characterized by its robust growth pattern, thicker leaves, fuller appearance and its inability to produce fruit.

4 Drawing Figures

The present invention relates to a new and distinct variety of olive tree.

The plant was discovered by me in 1962 as a chance seedling growing on my property at Glendora, Calif. The seed parent of the new variety is an unpatented variety of *Olea europaea* known as "Manzanillo". The "Manzanillo" variety is widely grown in California. However, it produces an abudance of fruit which ripen and drop in large numbers and this restricts the use of the "Manzanillo" variety as an ornamental.

The new variety has been asexually reproduced by me on the property of Olle Olsson Nursery, Inc., at 2154 Peck Rd., Monrovia, Calif. by means of cuttings. A large number of plants of the new variety have been reproduced by this method and in all cases the resulting plants have exhibited the distinguishing characteristics of the parent plant, indicating that the new variety is established.

The new variety as compared with the "Manzanillo" variety is characterized by an overall more robust growth pattern, thicker leaves, a fuller appearance and, significantly, a lack of fruit. It also differs from another fruitless olive tree, U.S. Plant Pat. No. 3,197 in that the new variety is a tetraploid.

Other distinctive characteristics of the new variety are exemplified in the accompanying illustrations.

Figure 1:
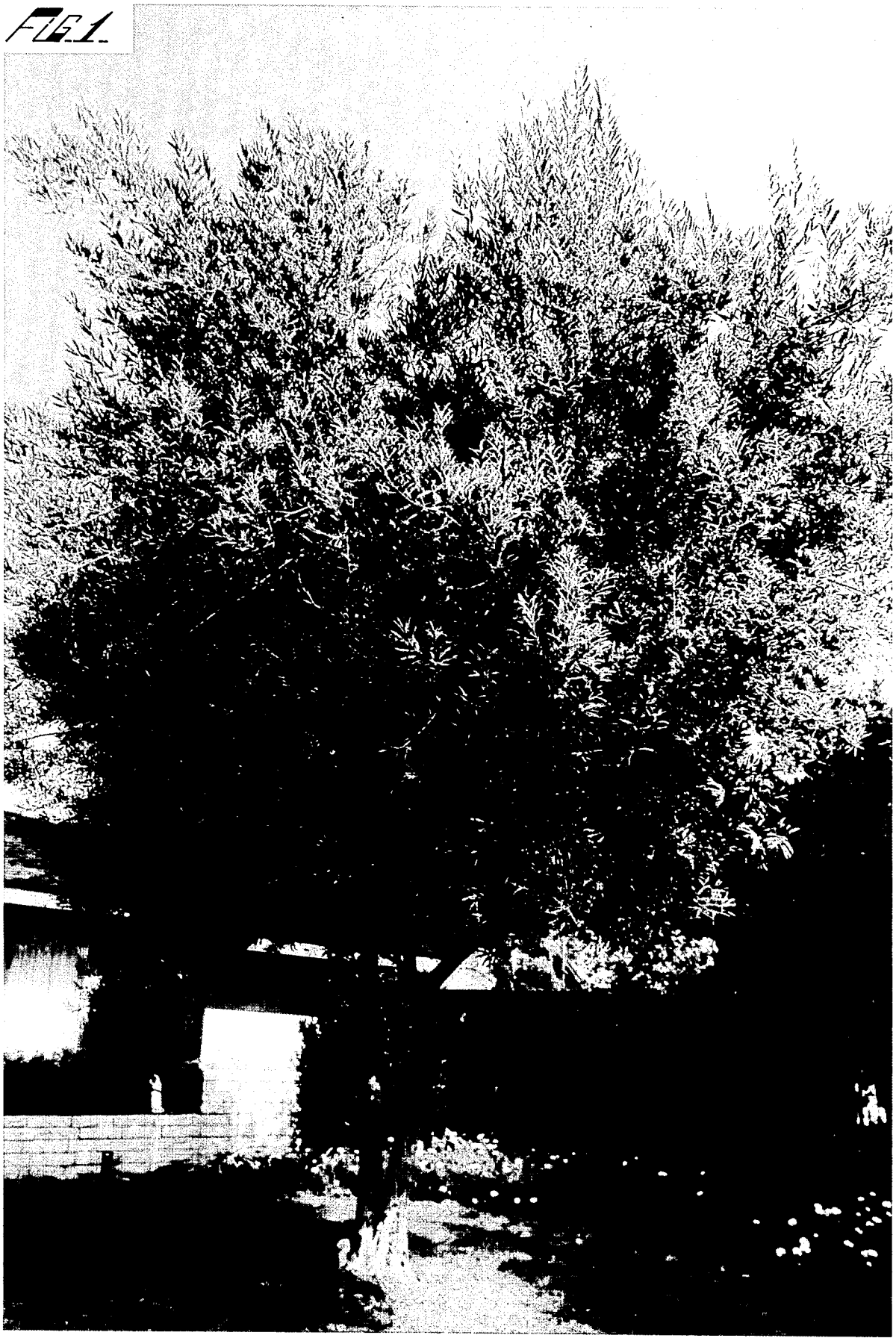
FIG. 1 shows the entire adult parent tree which grew from the original seedling.
Figure 2:
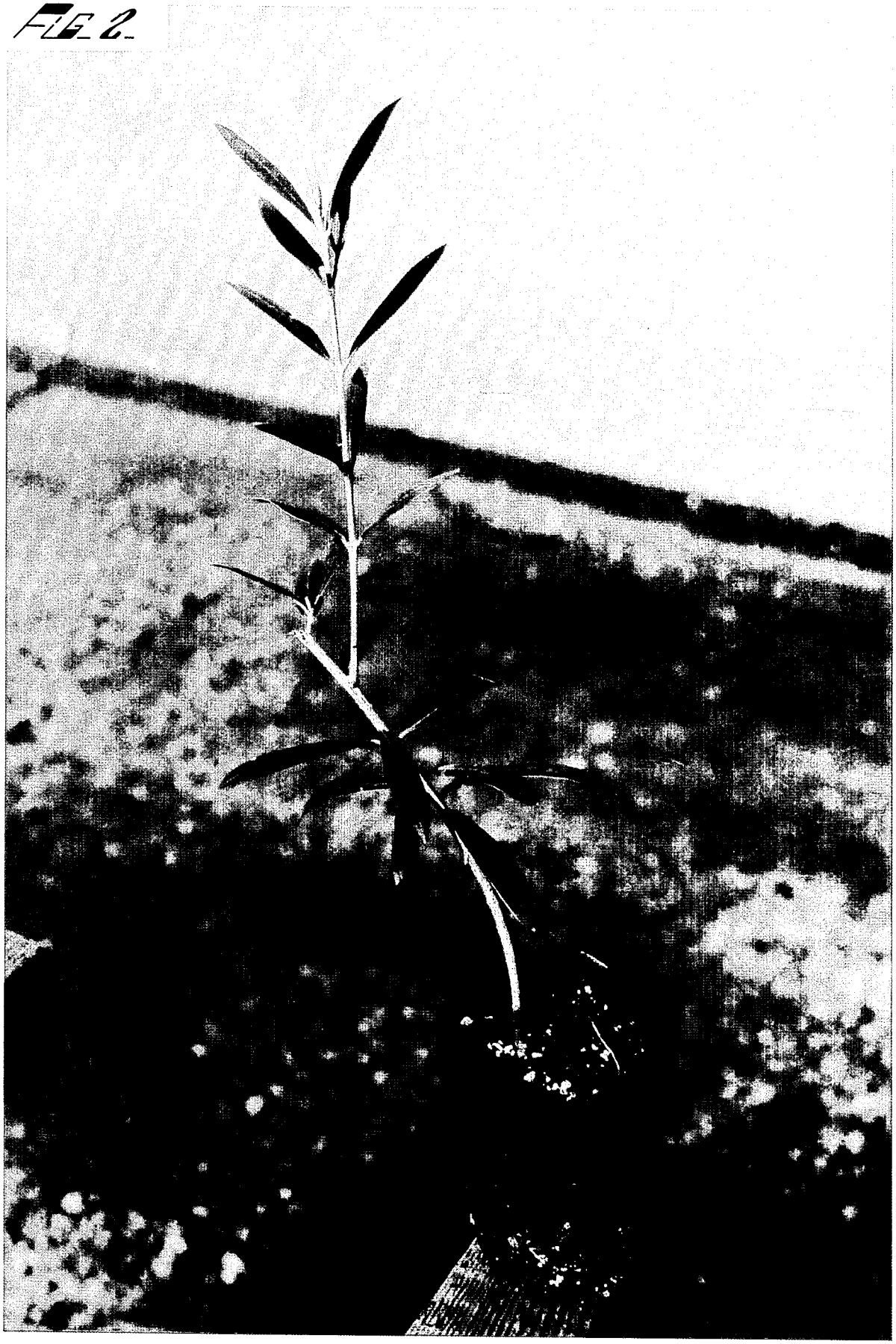
FIG. 2 shows a young tree.
Figure 3:
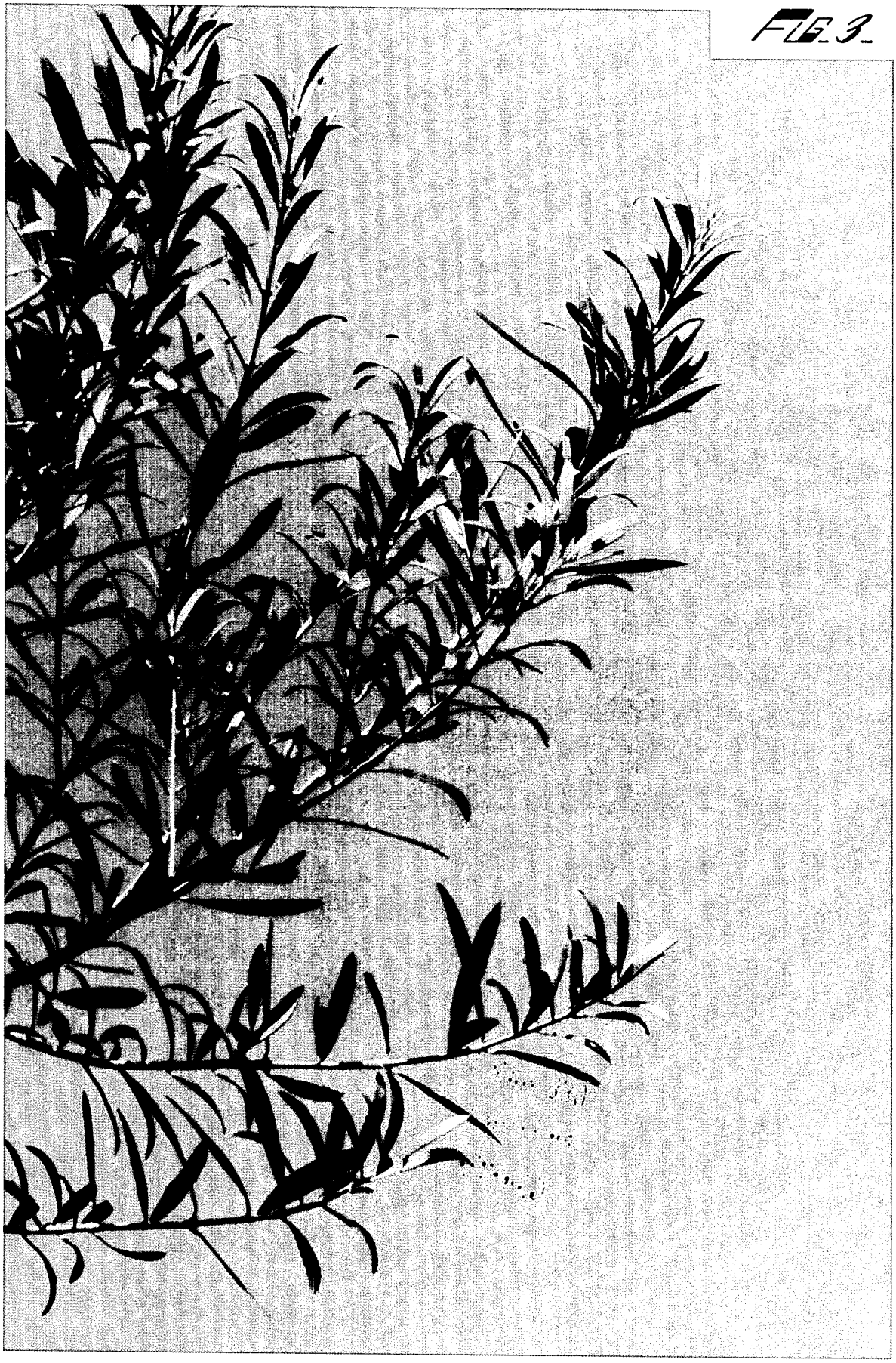
FIG. 3 shows a typical branch of the adult tree.
Figure 4:
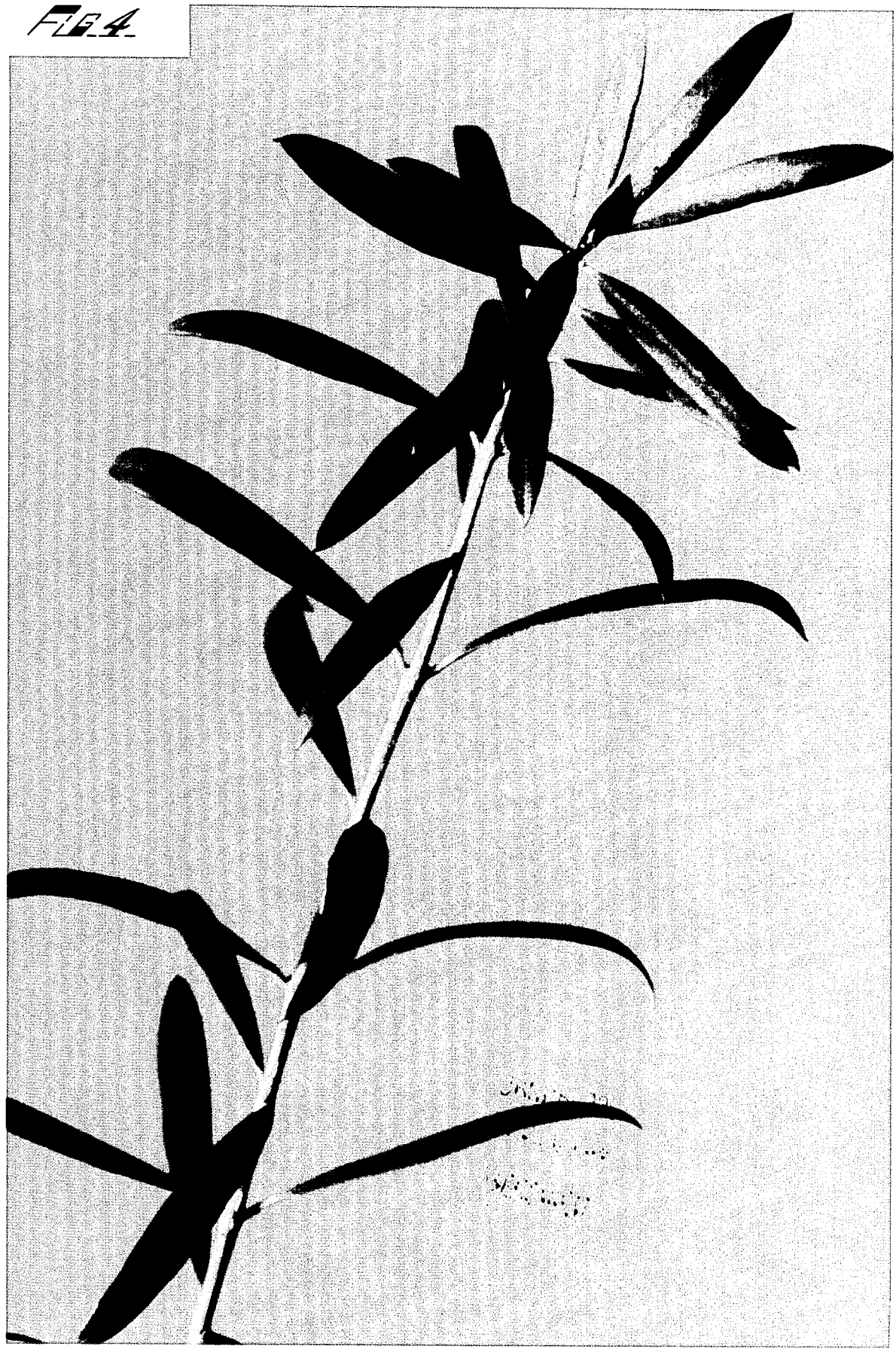
FIG. 4 is a close up of the leaves of the tree.

The illustrations closely approximate the colors of the tree, but to further facilitate the identification of the important colors reference is made to the British Horticultural Colour Charts in the description of the new variety.

Tree:

*Shape.*—Tree is upright with wide spreading crown, which is rounded in appearance.

*Size.*—Tree grows to approximately 7.5 meters in height with a branch spread of about the same as the height.

*Growth.*—Robust, dense; vigorous branches tend to arch prominently above and beyond the tree's general periphery.

Wood, current growth:

*Surface texture.*—Smooth at first, but with frequent lenticels.

*Color.*—Leaves silvery scaly underneath and dark green above.

Wood, medium age growth:

*Surface texture.*—Smooth with prominent lenticels. Lenticels become unusually prominent, large and elliptical in shape very rapidly.

*Color.*—Bark is grayish brown.

Wood, old growth:

*Surface texture.*—Lenticels become more prominent and very rough.

*Color.*—Color becomes more brown with age.

Leaves:

*Size.*—Thicker than the leaves on the "Manzanillo" variety. When mature, leaves usually range from 4.5 centimeters to 5 centimeters long and from 1 centimeter to 1.5 centimeters wide.

*Shape.*—Leaf shape is elliptical and obtuse, base slenderly cuneate.

*Color.*—Leaf color is dark green, glabrous and shiny above and silvery scaly underneath, both in immature and mature stages.

*Petiole.*—From 3 millimeters to 6 millimeters long; somewhat smaller caliper than in the "Manzanillo" variety.

*Margin.*—The margin of the leaf is entire.

*Arrangement.*—The leaves are opposite on the stem.

Flower:

*Size.*—Slightly larger than those of the "Manzanillo" variety in both length and diameter.

*Season.*—The season of flowering in the Glendora area is April through June.

*Color.*—The color of the flower is white or off-white.

*Pistils.*—The pistil is usually non-existent, but when occurring is deformed and abscises before maturity.

The above described new variety of olive tree has an evergreen foliage which is very attractive and has a fuller appearance than that of the "Manzanillo" variety. The fruitless characteristic of this new variety makes it particularly desirable for use as an ornamental since this eliminates the problem of the dropping of fruit which, if stepped on, can cause a staining of an adjacent patio or sidewalk.

I claim:

1. A new and distinct variety of olive tree as described and shown herein, characterized particularly by its more robust growth pattern, its thicker leaves and its fuller appearance, all as compared with the Manzanillo variety, and by its lack of fruit.

* * * * *